(12) United States Patent
Compton et al.

(10) Patent No.: US 6,500,633 B1
(45) Date of Patent: Dec. 31, 2002

(54) METHOD OF DETECTING CARCINOMAS

(75) Inventors: Timothy R. Compton, Irvine, CA (US); Jeff A. Parrott, Irvine, CA (US); James R. Erickson, El Cerrito, CA (US); Robert L. Wolfert, Tustin, CA (US)

(73) Assignee: Atairgin Technologies, Inc., Irvine, CA (US)

( * ) Notice: Subject to any disclaimer, the term of this patent is extended or adjusted under 35 U.S.C. 154(b) by 0 days.

(21) Appl. No.: 09/558,880

(22) Filed: Apr. 26, 2000

(51) Int. Cl.$^7$ ................................................. C12Q 1/32
(52) U.S. Cl. ......................................... 435/26; 436/813
(58) Field of Search .......................... 435/26, 4, 6, 7.9, 435/25; 436/63, 813; 536/23.5, 24.3

(56) References Cited

U.S. PATENT DOCUMENTS

| | | | |
|---|---|---|---|
| 4,693,971 A | | 9/1987 | Misaki |
| 4,698,299 A | | 10/1987 | Janoff et al. ................... 435/13 |
| 4,724,204 A | * | 2/1988 | Steinbach et al. ............. 435/26 |
| 5,122,454 A | | 6/1992 | Ueda et al. .................... 435/15 |
| 5,277,917 A | | 1/1994 | Xu et al. ...................... 424/537 |
| 5,326,690 A | | 7/1994 | Xu et al. ....................... 435/29 |
| 5,489,580 A | | 2/1996 | Makriyannis et al. ......... 514/10 |
| 5,824,555 A | * | 10/1998 | Xu et al. ....................... 436/64 |
| 5,994,141 A | * | 11/1999 | Xu et al. ....................... 436/64 |

FOREIGN PATENT DOCUMENTS

| | | | |
|---|---|---|---|
| BE | 882048 | | 9/1980 |
| EP | 0 322 262 | | 6/1989 |
| JP | 2-107195 | | 4/1990 |
| JP | 8-53475 | | 2/1996 |
| WO | WO 89/01773 | | 3/1989 |
| WO | WO 90/10448 | | 9/1990 |
| WO | WO 93/11136 | | 6/1993 |
| WO | WO 97/45727 | | 4/1997 |
| WO | WO 00/23612 | * | 4/2000 |
| WO | WO 01/32916 A2 | | 11/2000 |

OTHER PUBLICATIONS

Bligh and Dyer, (1959, "A rapid method of total lipid extraction and purification," *Can J. Biochem. Physiol.* 37(8):911–917.

Blusztajn, J.K., et al, "Levels of phospholipid catabolic intermediates, glycerophosphocholine and glycerophosphoethanolamine, are elevated in brains of Alzheimer's disease but not of Down's syndrome patients," *Brain Research*, 536 (1990) 240–244.

Dorum et al., (1996), "Early detection of familial ovarian cancer," *E. J. Cancer* 32A (10): 1645–1651.

Einhorn et al., (1992), "Prospective evaluation of serum CA 125 levels for early detection of ovarian cancer," *Obstet. Gynecol.* 80:14–18.

Fallbrook A., et al, "Phosphatidylcholine and phosphatidylethanolamine metabolites may regulate brain phospholipid catabolism via inhibition of lysophospholipase activity," *Brain Research* 834, (1999) 207–210.

Fukami, et al., (1988), "Antibody to phosphatidylinositol 4,5-bisphosphate inhibits oncogene-induced mitogenesis," *Proc. Natl. Acad. Sci. USA* 85:9057–9061.

Gregor Devc, ed., *Phospholipids Handbook*, Ch. 28: Gupta, "Phospholipids in Disease," pp. 895–908, 1993.

Holmes, Todd C., et al. "Phospholipid and Phospholipid Metabolites in Rat Frontal Cortex Are Decreased following Nucleus Basalis Lesions," *Ann. NY Acad. Sci.* 1993, 695:241–3.

Jacobs et al., (1996), "Risk of diagnosis of ovarian cancer after raised serum CA 12s concentration: a prospective cohort study," *BMJ* 313:1355–1358.

Jalink et al., (1994), "Growth factor–like effects of lysophosphatidic acid, a novel lipid mediator," *Biochim. Biophys. Acta* 1198:185–196.

Kalnova (1989), "Relationship between antioxidant activity and lipid profile of blood as marker of the effect of tumor on the host," *Vopr. Onkol* 35(7):795–801 abstract only.

Kriat et al., (1993), "Analysis of plasma lipids by NMR spectroscopy: Application to modifications induced by malignant tumors," *J. Lipid res.* 34:1009–1019.

Kume and Gimbrone, (1994), "Lysophosphatidylcholine transcriptionally induces growth factor gene expression in cultured human endothelial cells," *J. Clin. Invest.* 93:907–911.

Lloret and Moreno, (1995), "$Ca^{2+}$ Influx, Phosphoinositide Hydrolysis, and Histamine Release Induced by Lysophosphatidylserine in Mast Cells," *J. Cell Physiol.* 165:89–95.

Mills et al., (1988), "A putative new growth factor in ascitic fluid from ovarian cancer patients: Identification, characterization, and mechanism of action," *Cancer Research* 48:1066–1071.

Mills et al., (1990), "Ascitic fluid from human ovarian cancer patients contains growth factors necessary for intraperitoneal growth of human ovarian adenocarcinoma cells," *J. Clin. Invest.* 86:851–855.

Moolenaar, (1995), "Lysophosphatidic acid signalling," *Current Opinion in Cell. Biol.* 7:203–210.

Moolenaar, (1995), "Lysophosphatidic acid, a multifunctional phospholipid messenger," *J. Biol. Chem.* 270(22):12949–12951.

Moolenaar et al, (1992), "Lysophosphatidic acid: A bioactive phospholipid with growth factor–like properties," *Rev. Physiol. Biochem. Pharmacol.* 119:47–65.

(List continued on next page.)

Primary Examiner—Ralph Gitomer
(74) Attorney, Agent, or Firm—Orrick Herrington & Sutcliffe LLP

(57) ABSTRACT

The present invention relates to methods of detecting carcinomas by measuring the level of a glycero compound, such as glycerol-3-phosphate, in a plasma, serum, or urine specimen from a patient. The method is particularly useful as a screening test for ovarian and breast carcinomas.

5 Claims, 3 Drawing Sheets

OTHER PUBLICATIONS

Muto et al., (1993), "Screening for Ovarian Cancer: The preliminary experience of a familiar ovarian cancer center," *Gynecologic Oncol. 51*:12–20.

Nakano et al., (1994), "Lysophosphatidylcholine upregulates the level of heparin–binding epidermal growth factor–like growth factor mRNA in human monocytes," *Proc. Natl. Acad. Sci. USA 91*:1069–1073.

Nitsch, R.M., et al. "Evidence for a membrane defect in Alzheimer disease brain," *Proc. Natl. Acad. Sci. USA*, vol. 89, pp 1671–1675, Mar. 1992.

Nitsch, R.M., et al. "Phospholipid metabolite levels are altered in cerebral cortex of patients with dominantly inherited olivopontocerebellar atrophy," *Neuroscience Letters*, 161 (1993) 191–194.

Okita et al., (19997), "Elevated Levels and altered fatty acid compositon of plasma lysophosphatidylcholine (LYSOPC) in ovarian cancer patients," *Int. J. Cancer 71*:31–34.

Panetti et al., (1997), "Endothelial cell mitogenesis induced by LPA: Inhibiton by thrombospondin–1 and thrombospondin–2," *J. Lab. Clin. Med. 129*:208–216.

Phillips and Dodge, (1967), "Composition of phospholipids and of phospholipid fatty acids of human plasma," *J. Lipid Res. 8*: 676–681.

Podo, Franco, "Nuclear Magnetic Resonance Analysis of Tumor Necrosis Factor–induced Alterations of Phospholipid Metabolites and pH in Friend Leukemia Cell Tumors and Fibrosarcomas in Mice." *Cancer Research*, 47, 6481–6489, Dec. 15, 1987.

Racenis et a., (1992), "The Acyl Dihydroxyacetone Phosphate Pathway Enzymes for Glycerolipid Biosynthesis are Present in the Yeast *Saccharomyces cerevisiae*, " *J. Bacteriol. 174*:5702–5710.

Sasaki et al., (1993), "Potentiation of diacylglycerol–induced activation of protein kinase C by lysophospholipids," *FEBS Letters 310*(1):47–51.

Schapira et al., (1993), "The effectiveness of ovarian cancer screening: A decision analysis model," *Ann. Intern. Med. 118*:838–843.

Shen et al., (1997), "Evaluation of lysophosphatidic acid (LPA) as a diagnostic marker for ovarian cancer and other gynecological cancers," *Clinical Chemistry 43*(6):577.

Skipski et al., (1967, "Lipid composition of human serum lipoproteins," *Biochem. J. 104*:340–352.

Tamori–Natori et al., (1986), "Metabolism of Lysophosphatidylserine, a Potentiator of Histamine Release in rat Mast Cells," *J. Biochem. (Tokyo) 100*(3):581–590.

Thomas and Holub, (1991), Eicosanoid–dependent and –independent formation of individual [$^{14}$C]stearoyl–labeled lysophospholipids in collage–stimulated human platelets,: *Biochim. Biophys. Acta 1081:92–98*.

Tigyi et al., 1994, Lysophosphatidic acid possesses dual action in cell proliferation,: *Proc. Natl. Acad. Sci. USA 91*:1908–1912.

Tokumura et al., 1986, "Involvement of lysophospholipase D in the production of lysophosphatidic acid in rat plasma," *Biochim. Biophys. Acta 875*:31–38.

Van den Bosch et al., 1974, "Phosphoglyceride Metabolism," *Ann. Rev. Biochem. 43*:243–277.

Vogt, 1960, "Darmerregende Aktivtät verschiedener Phosphatide und Glykolipide," *Arch exp. Path. U. Pharmak. 240*:134–139.

Xu et al., (1995), "Lysophospholipids activate ovarian and breast cancer cells," *Biochem J. 309*:933–940.

Xu et al., (1995), "Characterization of an ovarian cancer activating factor in ascites from ovarian cancer patients[1]," *Clin. Cancer Res. 1*:1123–1232.

Xu et al., (1995), "Effect of Lysophospholipids on Signaling in the Human Jurkat T Cell Line," *J. Cell Physiol 163*: 441–450.

Zhou, Jianhui et al., "Identification of the First Mammalian Sphingosine Phosphate Lyase Gene and Its Functional Expression in Yeast," Biomedical and Biophysical Research Communications, 242, 502–507 (1998) Article No. RC977993.

* cited by examiner

METHOD OF DETECTING CARCINOMAS

FIELD OF THE INVENTION

The present invention relates to methods of detecting carcinomas by measuring the level of a glycero compound, such as glycerol-3-phosphate, in a plasma, serum, or urine specimen from a patient. The method is particularly useful as a screening test for ovarian and breast carcinomas.

BACKGROUND OF THE INVENTION

Carcinomas such as ovarian carcinoma, lung carcinoma, colon carcinoma, and breast carcinoma are among the most frequent causes of cancer death in the United States and Europe. Despite decades of cancer research, mortality rates among persons who contract cancer remain high. This dismal outcome is due, at least in part, to an inability to detect the carcinoma at an early stage of tumor development. When a carcinoma is detected at an early stage, survivability increases dramatically. For example, when ovarian carcinoma is diagnosed at an early stage, the cure rate approaches 90%. In contrast, the 5 year outlook for women with advanced disease remains poor with no more than a 15% survival rate. Thus, early diagnosis is one of the most effective means of improving the prognosis for carcinomas.

Frequently, however, detection of carcinomas depends upon the detection and inspection of a tumor mass which has reached sufficient size to be detected by physical examination. For instance, transvaginal sonography is the most sensitive of the currently available techniques used for detecting ovarian tumors. However, transvaginal sonography is non-specific, i.e. it will detect benign as well as malignant tumors. Accordingly, detection of an ovarian tumor by transvaginal sonography must be followed by a second diagnostic procedure which is able to distinguish benign tumors from malignant tumors. Moreover, transvaginal sonography is very expensive and, therefore, not useful as a screening procedure for large numbers of patients.

Typically, benign ovarian tumors are distinguished from malignant ovarian tumors by surgical procedures such as biopsy of the mass or aspiration of the mass and cytological examination of the cells that are surgically removed from the patient. However, these techniques are highly invasive, expensive, and in the case of aspiration can lead to release of cancerous cells into the peritoneum.

As can be seen from this example for ovarian cancer, several factors prevent the early detection and treatment of carcinomas. First, the carcinoma may be too small to be felt or seen on an x-ray or sonogram. Second, once the carcinoma is located, it may be mischaracterized as benign by the histologist examining a biopsy from the tumor. Third, the intensely invasive nature of these procedures prevents their use by patients and prohibits their use as regular screening techniques.

The detection of molecular markers of carcinogenesis and tumor growth can solve many of the problems which the physical examination of tumors have encountered. Samples taken from the patient for screening by molecular techniques are typically blood or urine, and thus require minimally invasive techniques. Thus, they can be used on a regular basis to screen for carcinomas. In addition, because molecular markers often appear before the tumor is of a detectable size, it is possible to detect carcinomas at very early stages in the progression of the disease. However, special processing of the samples is often required, and the molecular marker used is often of limited specificity and diagnostic value.

For instance, the antigenic determinant CA 125, which is a high molecular weight mucin-like glycoprotein, is the current serum biomarker of choice for screening for ovarian carcinomas. However, CA 125 testing suffers from two main limitations. First of all, it is not very sensitive. For example, elevated serum CA 125 levels, i.e. levels above the cut-off point of 35 U/ml, are present in fewer than 50% of the patients with Stage I ovarian carcinoma. Taylor, K. J. W. and Schwartz, P. E., "Screening for Early Ovarian Cancer," Radiology, 192:1–10, 1994. In addition, CA 125 testing is not very specific. For example, approximately 25% of patients with benign gynecological diseases also have elevated serum levels of CA 125. Moreover, liver disease such as cirrhosis, even without ascites, elevates serum CA 125 levels above 35 U/ml. Taylor, K. J. W. and Schwartz, P. E., "Screening for Early Ovarian Cancer," Radiology, 192:1–10, 1994.

Additionally, the level of lysophosphatidic acid (LPA) in the blood of patients has been used as an indicator of ovarian cancer and other gynecological carcinomas. For example, see the method disclosed in Xu, et al., U.S. Pat. Nos. 5,824,555, and 5,994,141. In this method, the plasma sample is first prepared from the blood of the patient. The sample may then be enriched by extracting lipids from the plasma sample with organic solvents in order to separate the LPA from other lipid components of blood. An LPA level of 0.1 $\mu$M or greater is then assayed in the sample in order to diagnose the patient as having an ovarian carcinoma. Although LPA concentration is conventionally determined by gas chromatography, LPA may also be measured by enzymatically converting LPA to glycerol-3-phosphate, and then determining the level of glycerol-3-phosphate produced from LPA by an enzymatic cycling assay, see WO 00/23612. Although levels of LPA and other lysophospholipids in the blood have been shown in the blood of patients with carcinomas, see WO 98/43093, no similar instance has been shown for the endogenous levels of glycero compounds such as glycerol-3-phosphate.

SUMMARY OF THE INVENTION

The present invention provides a new, simple method for detecting the presence of carcinomas in a patient. The method comprises detecting the presence of an endogenous glycero compound such as glycerol-3-phospate (G3P) or a glycero compound derivative thereof (GPX) in a plasma, serum, or urine sample of the patient at levels which correlate with the presence of a carcinoma.

An embodiment of the method comprises: collecting a serum, plasma, or urine specimen from the patient, assaying for the presence of G3P, GPX, or a combination of glycero compounds in the specimen, and correlating the presence of the glycero compound at levels indicative of a carcinoma with the presence of the carcinoma in the patient. Glycero compounds suitable for assaying in the present invention include glycerol-3-phosphate (G3P), glycerophosphoinositol (GPI), glycerophosphocholine (GPC), glycerophosphoserine (GPS), glycerophosphoglycerol (GPG), and glycerophosphoethanolamine (GPE). In preferred embodiments of the invention, the "glycero compound" assayed is a combination of these glycero compounds. A preferred embodiment of the method assays for the presence of the glycero compounds by an enzymatic cycling reaction utilizing glycerol-3-phosphate dehydrogenase and glycero-3-phosphate oxidase. If non-G3P glycero compounds are assayed in the invention, it is preferred that the enzymatic cycling reaction step be proceeded by an enzymatic step which cleaves non-G3P glycero compounds in the specimen to produce G3P.

The method of the present invention can be used to detect a broad range of carcinomas at an early stage, including breast carcinoma, ovarian carcinoma, cervical carcinoma, uterine carcinoma, endometrial carcinoma, peritoneal carcinoma, and fallopian tube carcinoma. Because the method is sufficiently sensitive to detect ovarian carcinoma in patients with early stage ovarian carcinoma and marginally invasive, the method is especially useful for screening patients for ovarian carcinomas. For the same reasons, the method is especially useful for screening patients for breast carcinomas, as current screening techniques (such as mammograms) are relatively expensive and uncomfortable for the patient.

DETAILED DESCRIPTION OF THE INVENTION

Figure 1:
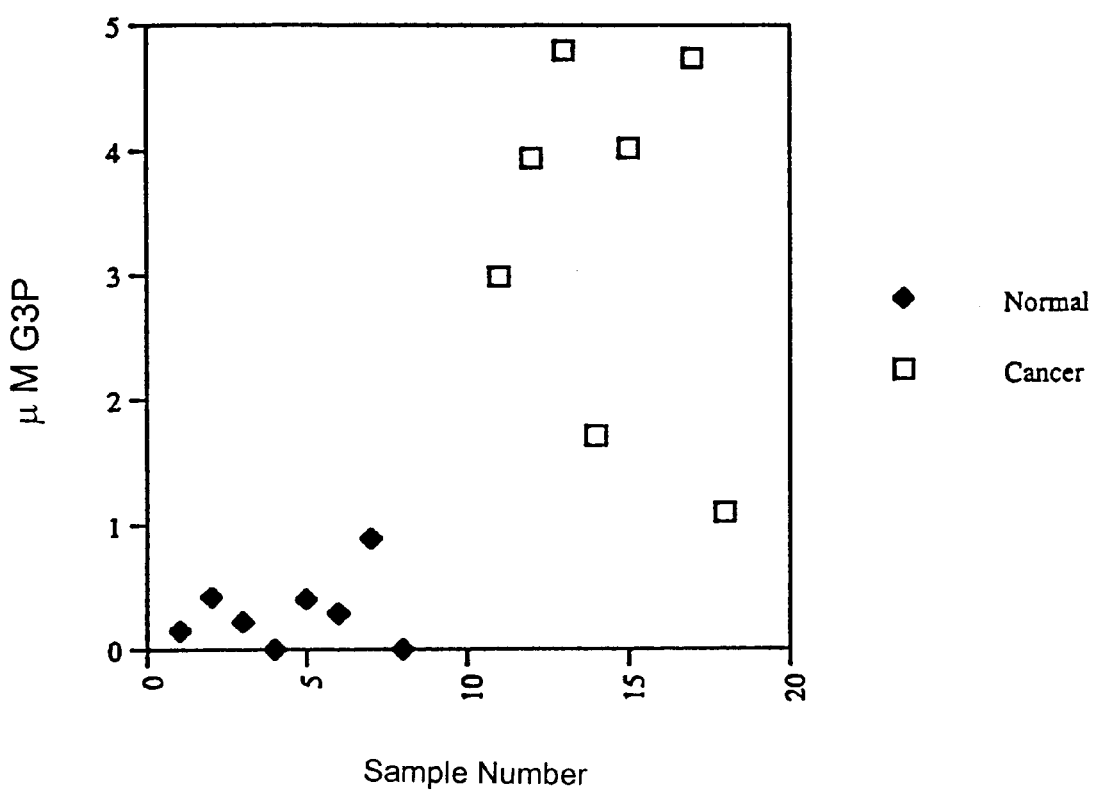
FIG. 1: A histograph of the level of G3P in plasma samples obtained from healthy patients and patients with an ovarian carcinoma.

The present invention provides a new, simple method for detecting the presence of a carcinomas, particularly ovarian carcinomas in, a patient. The method comprises detecting the presence of endogenous G3P, GPX, or a combination of glycero compounds in a serum, plasma, or urine sample from the patient. In a preferred embodiment, the method comprises providing a whole blood specimen from the patient, obtaining a serum or plasma specimen from the blood specimen, detecting the presence of endogenous G3P, GPX, or a combination of glycero compounds in the serum or plasma specimen, and correlating the presence of endogenous G3P, GPX, or a combination of glycero compounds at levels indicative of a carcinoma with the presence of a carcinoma in the patient.

As used herein, "endogenous glycero compound" or "endogenous glycerol-3-phosphate (G3P)" means that the glycero compound is present in the specimen as obtained from the patient, or as developed in the specimen without further treatment. Glycero compounds produced by enzymatic treatment of a specimen are explicitly considered non-endogenous. Glycero compounds suitable for assaying in the present invention include glycerol-3-phosphate (G3P) and glycero compound derivatives thereof (GPX). These derivatives typically have a substituent bound to the phosphate group of G3P, and include glycerophosphoinositol (GPI), glycerophosphocholine (GPC), glycerophosphoserine (GPS), glycerophosphoglycerol (GPG), and glycerophosphoethanolamine (GPE). In preferred embodiments of the invention, the "glycero compound" assayed is a combination of these glycero compounds.

Preferably, if a plasma specimen is used in the invention, the plasma sample is obtained under conditions which minimize the activation of platelets which are present in the whole blood specimen, which reduces endogenous enzymatic activity. Such conditions include, for example, collecting the whole blood specimen from the patient in tubes that contain an anti-coagulant. Suitable anti-coagulants include, for example, heparin and chelating agents. It is preferred that the whole blood specimen be collected in the presence of a chelating agent, such as for example ethylenediaminetetraacetic acid (EDTA) or sodium citrate, more preferably EDTA, since chelating agents both reduce endogenous enzyme activity in the sample and prevent clotting of the whole blood specimen. Preferably, if a plasma sample is used, the blood plasma sample is substantially free of platelets.

A serum sample may be obtained from a whole blood sample by standard procedures, such as centrifuging the whole blood sample at 500×g for 3 minutes, or at 3000×g for 15 minutes. A plasma sample typically is obtained by centrifuging the whole blood specimen to pellet the blood cells in the whole blood specimen and collecting the supernatant, which represents the major portion of the blood plasma in the whole blood specimen. Preferably the speed of this centrifugation step is between 400 to 1000×g. Optionally, higher speeds of 2000 to 3000×g may be used to more thoroughly pellet platelets in the specimen. Urine specimens may be collected in the conventional manner for use in the present invention.

The amount of endogenous G3P, GPX, or a combination of glycero compounds in the specimen is then quantified using conventional or enzymatic techniques. The quantification technique used depends upon the amount of specimen provided by the patient. For example, if the size of the blood specimen is 2 ml or less, it is preferred that a quantification technique which is capable of detecting picomole amounts of the glycero compound be used. Suitable conventional techniques for detecting picomole amounts of the glycero compound include, for example, quantifying the amount of each species in the sample by mass spectrometry. More preferred embodiments of the method of the invention utilize an enzymatic cycling reaction to detect the glycero compound.

These embodiments of the present invention utilize the following assay technique to measure G3P, GPX, or a combination of glycero compounds in the sample. A biological sample such as serum, plasma, or urine is collected from a patient. Then, at least one enzymatic digestion is performed to produce a detectable product. In a preferred embodiment, an enzyme cycling reaction which consists of two enzymatic reactions that accumulates detectable reduction-oxidation reaction products is performed. It is especially preferred that an enzyme cycling reaction using glycerol-3-phosphate dehydrogenase (GDH), glycerol-3-phosphate oxidase (GPO) and NADH to accumulate $H_2O_2$ and NAD (U.S. Pat. No. 5,122,454, Ueda et al.) be used in the invention. In this embodiment, G3P is converted to dihydroxyacetone phosphate (DAP) and hydrogen peroxide using G3P oxidase in the presence of oxygen and water. In the presence of DAP, G3P dehydrogenase converts dihydroxyacetone phosphate back to G3P and oxidizes NADH to NAD. The disappearance of NADH is monitored spectrophotometrically at $OD_{340}$. Alternatively, the production of hydrogen peroxide may be measured, for example: colorimetrically, by fluorometry, or by chemiluminescence. For a colorimetric assay any of a number of chromogenic substrates may be used including 4-aminoantipyrine (AAP), pyrogallol, 2-($2^1$-Azinobis (3-ethylbenzthiazoline-sulfonic acid)(ABTS) and 3,$3^1$,5,$5^1$-tetramethylbenzidine) (TMB).

It should be noted that in these embodiments, the endogenous level of both G3P and DAP are measured in the cycling reaction. For the purposes of this invention, DAP is considered to be a converted form of G3P, and in equilibrium in the sample. Thus measurement of total G3P and DAP is considered to be a measurement of G3P in this embodiment. However, it may be considered advantageous to measure only G3P or DAP in a sample by some other detection method. These embodiments are also considered to be within the scope of the present invention.

The level of G3P is detected by monitoring the oxidation of NADH spectrophotometrically at 340 nm (i.e. disappearance of $OD_{340}$) and the accumulation of $H_2O_2$ colorimetrically using peroxidase. Numerical values are obtained from a standard curve consisting of known concentrations of G3P. Typical standard curves include known amounts of G3P from 0 to 25 $\mu$M. Assays are preferably performed in duplicate with both positive and negative controls. The difference between $OD_{340}$ or $OD_{505}$ before and after the enzyme cycling reaction is directly proportional to the amount of G3P present. Background signals in the specimen without the cycling enzyme mix are subtracted from all samples. G3P standard curve values are plotted and fitted to a linear or second-order polynomial curve fit. The levels of G3P in each sample are determined by comparing each signal measured to the standard curve.

If a non-G3P glycero compound is to be assayed in the method of the present invention, it is preferable that the assay comprise two enzymatic steps. First, an enzyme is utilized to cleave the non-G3P glycero compounds in the sample to produce G3P, and then the sample is assayed as above for total G3P content. Thus, the G3P measured will be: [endogenous G3P]+[G3P produced by enzymatic cleavage]. The sample is preferably first digested using glycerophosphatidyl compound phosphodiesterase (GPX-PDE) to cleave the substituent from the phosphate of the G3P backbone. The applicants have found that enzymes marketed as glycerophosphatidylcholine phosphodiesterase (GPC-PDE) have a non-specific activity which cleaves all GPX species at the phosphate-substituent bond. Total G3P may then be measured according to the enzymatic cycling reaction described above.

In alternate embodiments of the invention, the substituents cleaved from the GPX species (i.e., inositol, glycerol, serine, choline, or ethanolamine) may be detected. In this way, the concentrations of specific GPX species in the sample may be used for the detection of carcinomas in the patient. Methods of enzymatically or instrumentally quantifying inositol, glycerol, serine, choline, or ethanolamine are well known in the art.

In order to optimize the detection of G3P, GPX, or a combination of glycero compounds, inhibitors of endogenous enzymes that may be present in the sample may be used to prevent degradation of the G3P, GPX, or a combination of glycero compounds levels in the sample. Such inhibitors include phosphodiesterase inhibitors such as IBMX (3-Isobutyl-1-methylxanthine, CalBiochem, La Jolla, Calif.); Ro-20-1724 (CalBiochem); Zaprinast (CalBiochem) and Pentoxifylline (CalBiochem); general protease inhibitors such as E-64 (trans-Epoxysuccinyl-L-leucylamido-(4-guanidino)butane, Sigma); leupeptin (Sigma); pepstatin A (Sigma); TPCK (N-tosyl-L-phenylalanine chloromethyl ketone, Sigma); PMSF (Phenylmethanesulfonyl fluoride, Sigma); benzamidine (Sigma) and 1,10-phenanthroline (Sigma); organic solvents including chloroform and methanol; detergents such as SDS or Trident X100; proteases that would degrade phospholipases such as trypsin (Sigma) and thermostable protease (Boehringer Mannheim Biochemicals, Indianapolis, Ind.); and metal chelators such as EDTA (Ethylenediaminetetracetic acid, Sigma) and EGTA (Ethylene glycol-bis-(beta-aminoethyl ether), Sigma).

The assay may be performed in a microtiter plate format to permit small volumes of samples and reagents to be employed and for monitoring, e.g. using an ELISA reader. These formats facilitate automating the performance of the assay. Reduced processing times for the assays using such formats may reduce variability between results. In addition, the methods of the present invention would be easily adapted for use in micro-scale automated assay equipment, such as the Immuno I system available from Bayer, the Access system available from Beckman Coulter, or the Dimension RxL HM system available from Dade Bahring.

The correlation of the level of G3P, GPX, or a combination of glycero compounds in the sample with the cancer state is usually specific for the type of sample and type of carcinoma. For instance, in the first example below, wherein a plasma sample is used, a level of G3P in the plasma sample of a patient which is greater than about 1 $\mu$M is indicative of an ovarian carcinoma in the patient. However, in the second example below, wherein a serum sample is used, a level of GPX+G3P in the serum sample of a patient which is less than about 40 $\mu$M is indicative of a breast carcinoma in the patient. The person of ordinary skill in the art would be capable of determining the proper level of G3P, GPX, or combination of glycero compounds in the sample which is indicative of a particular disease state, given the guidance supplied by this specification and the examples below, utilizing routine experimentation. For instance, one of ordinary skill in the art would know to first establish an positive indicator threshold level of the glycero compound for a particular sample technique (serum, plasma, or urine) by first comparing samples taken from normal patients with those diagnosed as having the particular carcinoma (breast carcinoma, ovarian carcinoma, cervical carcinoma, uterine carcinoma, endometrial carcinoma, peritoneal carcinoma, and fallopian tube carcinoma.) By making such a comparison, utilizing samples available from various specimen banks and the assay techniques detailed below, one may establish the proper indicative threshold to diagnose a patient as having a particular type of carcinoma. In general, plasma samples prepared as in Example 1 which have a higher than normal level of G3P, GPX, or a combination thereof, will indicate the presence of a carcinoma, while serum samples prepared as in Example 2 which have a lower than normal level of G3P, GPX, or a combination thereof, will indicate the presence of a carcinoma.

In addition to its use as a detection method, the response of a condition to treatment may be monitored by determining concentrations of G3P, GPX, or a combination of glycero compounds in samples taken from a patient over time. The concentration of G3P, GPX, or a combination of glycero compounds is measured and compared to the concentration taken at the earlier time from that patient. If there is a significant change in the concentration of G3P, GPX, or a combination of glycero compounds, over time, it may indicate an increase in the severity of the condition in the patient. Conversely, if there is a normalization of the concentration of G3P, GPX, or a combination of glycero compounds, it may indicate an improvement in the condition of the patient.

The methods described herein for measuring concentrations of G3P, GPX, or a combination of glycero compounds in samples of bodily fluids from a patient may also be performed, for example, by using pre-packaged diagnostic kits. Such kits include reagents for the cleavage of non-G3P glycero compounds to produce G3P. Other reagents in the kits include those to perform the enzyme cycling reaction such as glycerol-3-phosphate dehydrogenase, glycerol-3-phosphate oxidase and β-nicotinamide adenine dinucleotide (NADH) and ancillary agents such as buffering agents, and agents such EDTA to inhibit subsequent degradation of G3P or GPX during transport or storage of the samples. The kits may also include an apparatus or container for conducting the methods of the invention and/or transferring samples to a diagnostic laboratory for processing, as well as suitable instructions for carrying out the methods of the invention.

The methods disclosed herein are simple, marginally invasive, and require only a blood or urine specimen from the patient. Thus, such methods are also useful for screening patients who have not been previously diagnosed as carrying carcinoma, particularly patients who are at risk for carcinomas, especially ovarian carcinoma or breast carcinoma. Such patients include women at elevated risk by virtue of a family history of the disease, premenopausal women with anovulatory cycles, and postmenopausal women.

Because of its sensitivity, simplicity, and low cost, the present method is useful for screening patients for carcinomas. Because the blood specimens for the present method and for CA 125 testing can be drawn from a patient at the same time, CA 125 testing can also be performed when patients are screened for carcinomas by the present methods. Alternatively, the present method can be used alone to detect carcinomas.

The present invention is further described by the examples which follow. Such examples, however, are not to be construed as limiting in any way either the spirit or the scope of the present invention.

EXAMPLES

Example 1
Assay of Plasma Specimen Levels of G3P for the Detection of Ovarian Carcinomas Plasma samples were obtained from blood specimens provided by fifteen female patients. A whole blood specimen was collected from each of the patients in a 5 ml vacutainer tube containing 15% EDTA. The whole blood specimen was centrifuged at 2500×g for 15 minutes to provide a pellet of the blood cells and platelets and a supernatant. The plasma supernatant was either processed immediately or stored at −70° C.

Endogenous G3P levels were then determined by enzymatic assay of the plasma samples as detailed below:

Reagents

Glycerol-3-phosphate oxidase, glycerol-3-phosphate dehydrogenase, human plasma, human serum, 4-aminoantipyrine (AAP) and calcium chloride were purchase from Sigma Chemical Co., St. Louis, Mo. Peroxidase and NADH were purchased from Boehringer Mannheim, Indianapolis, Ill. All lipid standards, fatty acids and methyl esters were purchased from Avanti Polar Lipids, Alabaster, Ala. or Sigma Chemical Co.

Enzyme Assay

In the well of a 96 well microtiter plate, 5 $\mu$l of the sample was distributed. 200 $\mu$L of cycling reaction enzyme mix containing 10 units of G3P dehydrogenase, 4 units of G3P oxidase, 0.34 mM NADH and 5 mM $CaCl_2$ in 50 mM Tris (pH 8.0) was added and the mixture incubated at 37° C. for 30 minutes. The G3P oxidase converts G3P to dihydroxyacetone phosphate and $H_2O_2$. The dihydroxyacetone phosphate was in turn converted back to G3P by G3P dehydrogenase. This reaction oxidizes NADH to NAD. Therefore, as cycling continues, both $H_2O_2$ and NAD accumulate.

The level of G3P was determined by monitoring the oxidation of NADH (i.e. the reduction of absorbance at 340 nm after the cycling action compared to $A_{340}$ before cycling). In addition, the accumulation of $H_2O_2$ was determined colorimetrically by adding 50 $\mu$l of a solution containing 0.5 units peroxidase, 0.5% HDCBS and 0.15% AAP in 50 mM Tris 8.0 to each well and recording the absorbance at 505 nm.

Numerical values for concentrations of G3P were obtained from a standard curve constructed from known G3P amounts. An internal standard of extracted plasma was included within each assay (i.e. each plate) that was measured at different dilutions. In some cases, this internal standard was used to correct for variations between different experiments. When the colorimetric method was used, the plate was blanked at 505 nm prior to color development.

The concentrations in $\mu$M of G3P in each of the samples are presented in Table 1, and in the histogram in FIG. 1. Each of the female patients also underwent one or more routine diagnostic procedures to determine whether she was healthy or had an active disease. The diagnostic procedures included, where appropriate, clinical examination, clinical chemistries, and surgical evaluation of any masses detected. On the basis of these routine diagnostic procedures, the patients were diagnosed as being healthy or as having ovarian cancer, as listed in Table 1.

TABLE 1

Level of G3P Assayed in Plasma

| Sample No. | Clinical Data | $\mu$M G3P |
| --- | --- | --- |
| 1 | Normal | 0.15 |
| 2 | Normal | 0.42 |
| 3 | Normal | 0.22 |
| 4 | Normal | 0.0 |
| 5 | Normal | 0.4 |
| 6 | Normal | 0.29 |
| 7 | Normal | 0.89 |
| 8 | Normal | 0.0 |
| 11 | Ovarian Cancer | 2.99 |
| 12 | Ovarian Cancer | 3.94 |
| 13 | Ovarian Cancer | 4.8 |
| 14 | Ovarian Cancer | 1.71 |
| 15 | Ovarian Cancer | 4.02 |
| 16 | Ovarian Cancer | 4.74 |
| 17 | Ovarian Cancer | 1.1 |

As shown in Table 1, higher than normal levels of G3P were found in each of the patients with ovarian carcinoma. No false negatives were observed in any of the patients with ovarian carcinoma. The concentration of G3P in patients with ovarian carcinoma ranged from 1.1 to 4.8 $\mu$M. The concentration of G3P in normal patients ranged from 0.0 to 0.89 $\mu$M. Moreover, the average concentration of G3P in the plasma of patients diagnosed as having ovarian carcinoma was significantly higher than the average concentration of G3P in the plasma of healthy patients. These results establish that the present method is highly sensitive and therefore useful for identifying those patients with the carcinoma of ovarian carcinoma.

Example 2
Assay of Serum Specimen Levels of G3P and GPX for the Detection of Ovarian Carcinomas Blood from 200 patients was collected in serum vacutainer tubes and allowed to clot at room temperature for up to 30 minutes. Clotted blood was centrifuged at about 500×g for 3–10 minutes. The serum sample supernatant was then withdrawn and kept at −70° C. until tested.

Enzymatic Assay

The samples were assayed for G3P as described in Example 1.

For the GPX+G3P assay, 5 µl of the sample was dispensed into the well of a 96 well microtiter plate. To each well, 100 µl of GPX-PDE (0.0125 Units) was added and incubated at 37° C. for 15 minutes. The GPX-PDE then liberates G3P and the substituent from phosphate substituted glycerophosphoro compounds. The plate was then blanked at the appropriate absorbance wavelength in the ELISA reader. Next, 100 µL of cycling reaction enzyme mix containing 10 units of G3P dehydrogenase, 4 units of G3P oxidase, 0.34 mM NADH and 5 mM $CaCl_2$ in 50 mM Tris (pH 8.0) was added and the mixture incubated at 37° C. for 30 minutes. The G3P oxidase converts G3P to dihydroxyacetone phosphate and $H_2O_2$. The dihydroxyacetone phosphate was in turn converted back to G3P by G3P dehydrogenase. This reaction oxidizes NADH to NAD. Therefore, as cycling continues, both $H_2O_2$ and NAD accumulate.

The level of G3P was determined by monitoring the oxidation of NADH (i.e. the reduction of absorbance at 340 nm after the cycling action compared to $A_{340}$ before cycling). In addition, the accumulation of $H_2O_2$ was determined colorimetrically by adding 50 µl of a solution containing 0.5 units peroxidase, 0.5% HDCBS and 0.15% AAP in 50 mM Tris 8.0 to each well and recording the absorbance at 505 mn.

Numerical values for concentrations of G3P were obtained from a standard curve constructed from known G3P amounts. An internal standard of extracted plasma was included within each assay (i.e. each plate) that was measured at different dilutions. In some cases, this internal standard was used to correct for variations between different experiments. When the colorimetric method was used, the plate was blanked at 505 nm prior to color development.

Figure 2:
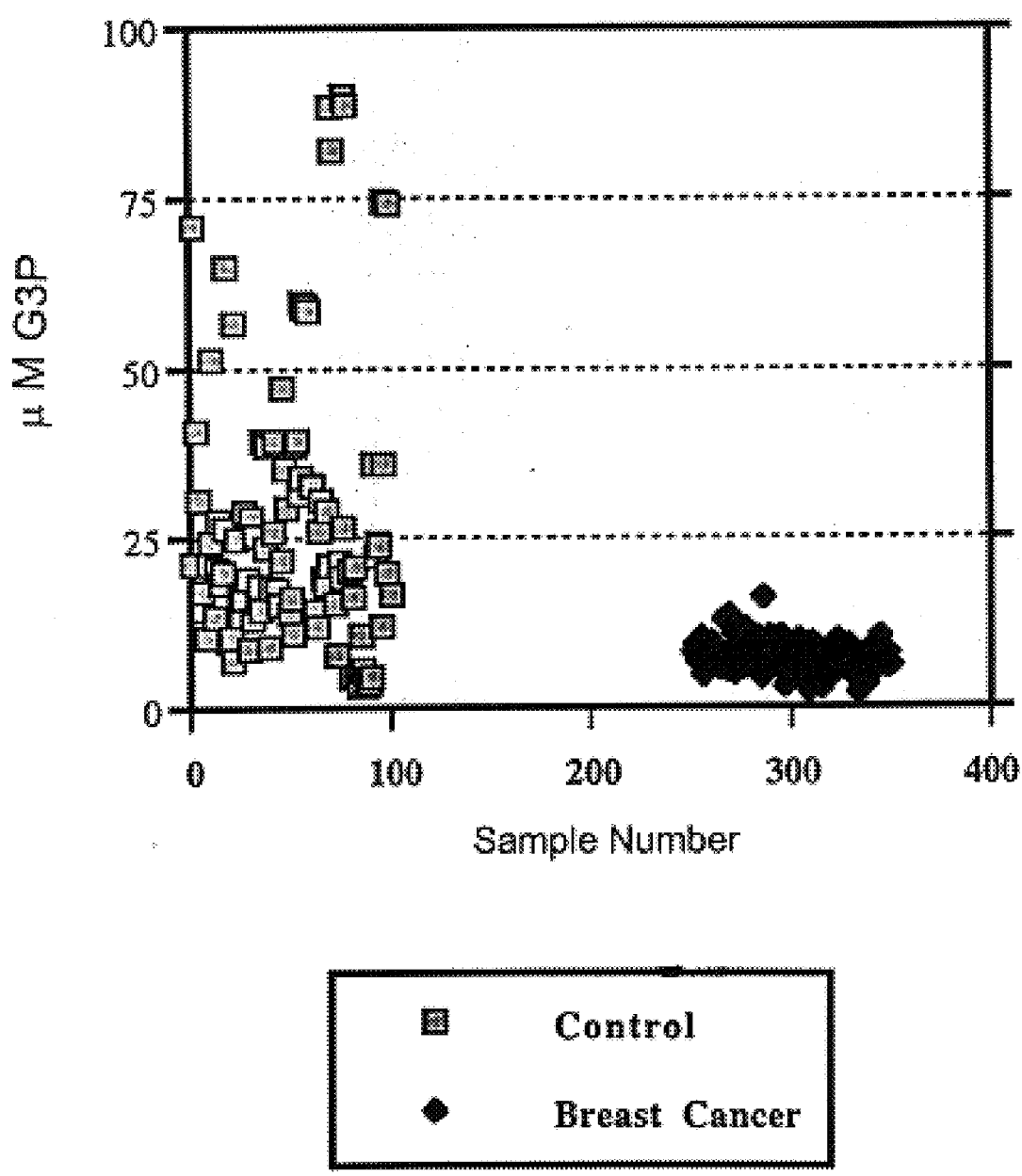
FIG. 2: A histograph of the level of G3P in serum samples obtained from healthy patients and patients with a breast carcinoma.
Figure 3:
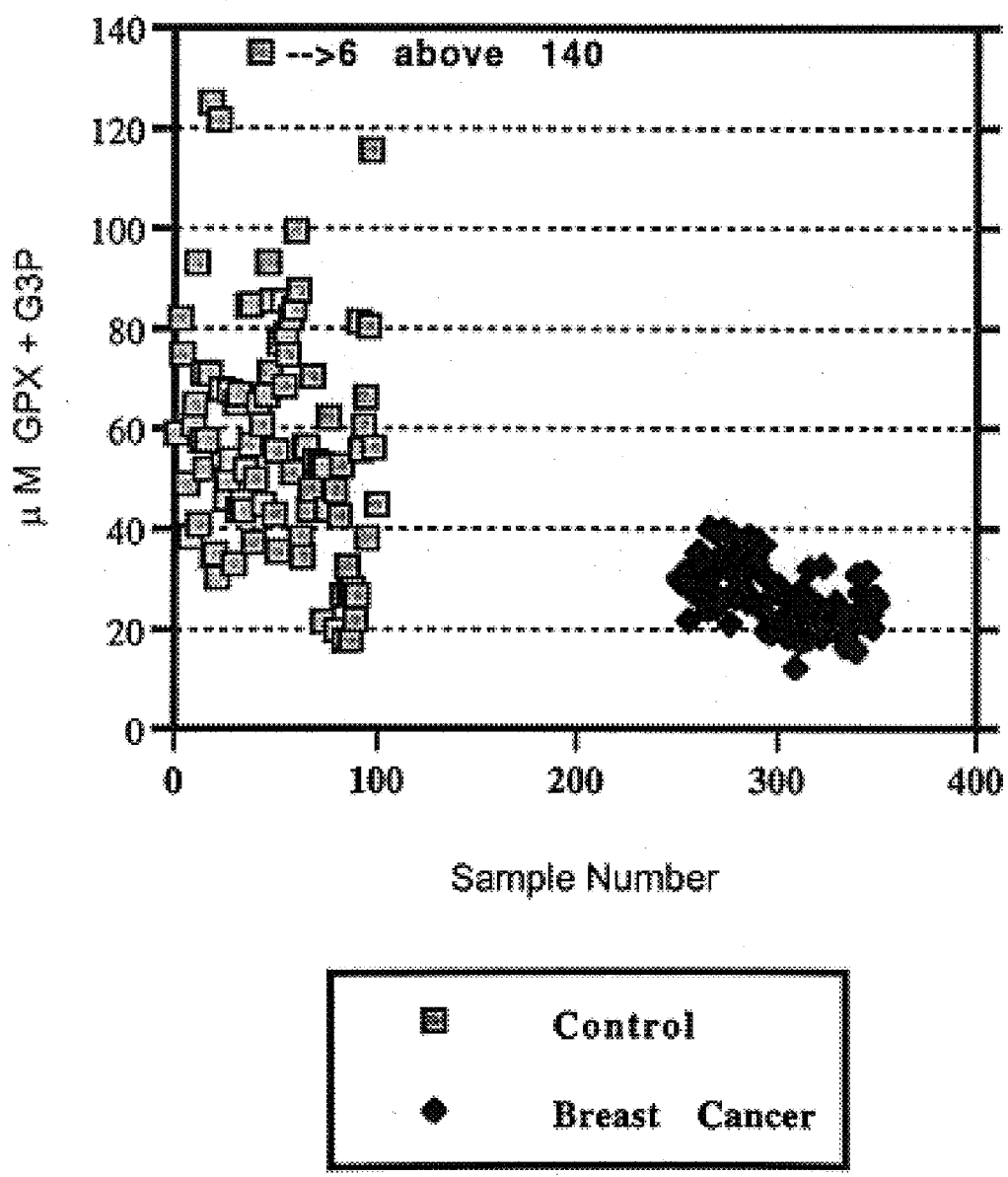
FIG. 3: A histograph of the level of GPX+G3P in serum samples obtained from healthy patients and patients with a breast carcinoma.

The concentrations in µM of G3P and GPX+G3P in each of the samples are presented in Tables 2 and 3, and in the histographs in FIGS. 2 and 3, respectively. Each of the female patients also underwent one or more routine diagnostic procedures to determine whether she was healthy or had an active disease. The diagnostic procedures included, where appropriate, clinical examination, clinical chemistries, and surgical evaluation of any masses detected. On the basis of these routine diagnostic procedures, the patients were diagnosed as being healthy or as having breast cancer. Patients from which samples 1–100 were drawn had negative breast tissue biopsies. Patients from which samples 250–350 were drawn had breast tissue biopsies positive for breast carcinoma.

TABLE 2

Level of G3P Assayed in Serum

| Sample | µM | Sample | µM | Sample | µM | Sample | µM |
|---|---|---|---|---|---|---|---|
| 1 | 21.2 | 58 | 59.4 | 264 | 5.7 | 321 | 5.9 |
| 2 | 70.9 | 59 | 58.5 | 265 | 6.2 | 322 | 5.0 |
| 3 | 40.8 | 60 | 32.9 | 266 | 12.8 | 323 | 9.8 |
| 4 | 30.5 | 61 | 32.6 | 267 | 6.9 | 324 | 9.7 |
| 5 | 10.8 | 62 | 14.3 | 268 | 5.5 | 325 | 8.5 |
| 6 | 17.1 | 63 | 12.0 | 269 | 13.5 | 326 | 8.9 |
| 7 | 11.3 | 64 | 26.0 | 270 | 7.0 | 327 | 8.6 |
| 8 | 10.4 | 65 | 30.5 | 271 | 10.9 | 328 | 8.5 |
| 9 | 21.2 | 66 | 18.9 | 272 | 5.1 | 329 | 9.1 |
| 10 | 24.5 | 67 | 18.1 | 273 | 8.7 | 330 | 8.4 |
| 11 | 51.4 | 68 | 29.0 | 274 | 9.3 | 331 | 4.6 |
| 12 | 13.4 | 69 | 20.9 | 275 | 8.2 | 332 | 5.7 |
| 13 | 20.6 | 70 | 88.3 | 276 | 5.8 | 333 | 7.0 |
| 14 | 27.5 | 71 | 82.0 | 277 | 11.6 | 334 | 2.2 |
| 15 | 18.3 | 72 | 15.3 | 278 | 8.0 | 335 | 4.4 |
| 16 | 19.9 | 73 | 7.8 | 279 | 7.4 | 336 | 3.1 |
| 17 | 26.3 | 74 | 21.5 | 280 | 11.0 | 337 | 6.3 |
| 18 | 65.0 | 75 | 19.1 | 281 | 9.5 | 338 | 3.4 |
| 19 | 9.9 | 76 | 26.6 | 282 | 6.7 | 339 | 4.4 |
| 20 | 10.3 | 77 | 89.9 | 283 | 10.2 | 340 | 8.7 |
| 21 | 7.0 | 78 | 88.6 | 284 | 6.9 | 341 | 7.1 |
| 22 | 56.8 | 79 | 20.1 | 285 | 4.5 | 342 | 8.0 |
| 23 | 24.8 | 80 | 4.5 | 286 | 16.2 | 343 | 7.2 |
| 24 | 16.7 | 81 | 16.3 | 287 | 6.5 | 344 | 6.4 |
| 25 | 13.7 | 82 | 20.7 | 288 | 9.6 | 345 | 10.3 |
| 26 | 16.1 | 83 | 4.7 | 289 | 10.4 | 346 | 7.7 |
| 27 | 28.9 | 84 | 3.2 | 290 | 8.6 | 347 | 8.1 |
| 28 | 19.0 | 85 | 10.7 | 291 | 9.4 | 348 | 6.0 |
| 29 | 8.7 | 86 | 5.6 | 292 | 6.1 | 349 | 7.9 |
| 30 | 28.0 | 87 | 3.2 | 293 | 10.2 | 350 | 6.1 |
| 31 | 13.2 | 88 | 4.3 | 294 | 5.8 | | |
| 32 | 25.3 | 89 | 3.6 | 295 | 10.4 | | |
| 33 | 15.7 | 90 | 4.6 | 296 | 5.5 | | |
| 34 | 18.0 | 91 | 35.9 | 297 | 3.2 | | |
| 35 | 14.4 | 92 | 22.3 | 298 | 9.2 | | |
| 36 | 39.4 | 93 | 24.1 | 299 | 8.6 | | |
| 37 | 23.6 | 94 | 23.8 | 300 | 7.5 | | |
| 38 | 38.6 | 95 | 11.9 | 301 | 5.3 | | |
| 39 | 8.9 | 96 | 35.9 | 302 | 4.6 | | |
| 40 | 17.6 | 97 | 74.5 | 303 | 8.5 | | |
| 41 | 25.8 | 98 | 19.7 | 304 | 9.8 | | |
| 42 | 39.4 | 99 | 74.2 | 305 | 4.7 | | |
| 43 | 17.5 | 100 | 16.6 | 306 | 6.8 | | |
| 44 | 15.2 | | | 307 | 9.3 | | |
| 45 | 21.7 | 251 | 8.1 | 308 | 7.0 | | |
| 46 | 47.2 | 252 | 9.2 | 309 | 2.4 | | |
| 47 | 35.3 | 253 | 6.8 | 310 | 9.5 | | |
| 48 | 29.4 | 254 | 8.3 | 311 | 3.6 | | |
| 49 | 13.9 | 255 | 10.3 | 312 | 9.1 | | |
| 50 | 16.2 | 256 | 4.8 | 313 | 5.6 | | |
| 51 | 11.0 | 257 | 9.6 | 314 | 5.8 | | |
| 52 | 38.6 | 258 | 8.0 | 315 | 2.8 | | |
| 53 | 39.4 | 259 | 7.6 | 316 | 5.4 | | |
| 54 | 31.4 | 260 | 9.6 | 317 | 7.2 | | |
| 55 | 34.0 | 261 | 9.4 | 318 | 5.0 | | |
| 56 | 59.7 | 262 | 8.6 | 319 | 4.8 | | |
| 57 | 59.0 | 263 | 6.1 | 320 | 7.2 | | |

TABLE 3

Level of GPX + G3P Assayed in Serum

| Sample | µM | Sample | µM | Sample | µM | Sample | µM | Sample | µM |
|---|---|---|---|---|---|---|---|---|---|
| 1 | 59 | 42 | 135 | 83 | 27 | 272 | 26 | 313 | 18 |
| 2 | 249 | 43 | 61 | 84 | 18 | 273 | 40 | 314 | 24 |
| 3 | 82 | 44 | 45 | 85 | 32 | 274 | 34 | 315 | 18 |
| 4 | 75 | 45 | 67 | 86 | 27 | 275 | 32 | 316 | 32 |
| 5 | 38 | 46 | 93 | 87 | 18 | 276 | 21 | 317 | 26 |
| 6 | 49 | 47 | 71 | 88 | 28 | 277 | 39 | 318 | 23 |
| 7 | 39 | 48 | 85 | 89 | 22 | 278 | 27 | 319 | 24 |
| 8 | 38 | 49 | 43 | 90 | 27 | 279 | 26 | 320 | 25 |
| 9 | 61 | 50 | 55 | 91 | 81 | 280 | 35 | 321 | 23 |
| 10 | 65 | 51 | 36 | 92 | 56 | 281 | 34 | 322 | 18 |
| 11 | 93 | 52 | 77 | 93 | 60 | 282 | 29 | 323 | 33 |
| 12 | 41 | 53 | 85 | 94 | 66 | 283 | 32 | 324 | 24 |
| 13 | 58 | 54 | 68 | 95 | 38 | 284 | 27 | 325 | 22 |
| 14 | 71 | 55 | 79 | 96 | 80 | 285 | 25 | 326 | 23 |
| 15 | 52 | 56 | 75 | 97 | 116 | 286 | 39 | 327 | 20 |
| 16 | 58 | 57 | 82 | 98 | 56 | 287 | 26 | 328 | 23 |
| 17 | 71 | 58 | 51 | 99 | 167 | 288 | 32 | 329 | 25 |
| 18 | 125 | 59 | 84 | 100 | 45 | 289 | 35 | 330 | 25 |
| 19 | 35 | 60 | 99 | | | 290 | 33 | 331 | 21 |
| 20 | 35 | 61 | 87 | 251 | 30 | 291 | 32 | 332 | 22 |
| 21 | 30 | 62 | 38 | 252 | 30 | 292 | 24 | 333 | 19 |
| 22 | 122 | 63 | 34 | 253 | 29 | 293 | 37 | 334 | 17 |
| 23 | 68 | 64 | 56 | 254 | 32 | 294 | 20 | 335 | 20 |
| 24 | 53 | 65 | 56 | 255 | 29 | 295 | 30 | 336 | 17 |
| 25 | 46 | 66 | 44 | 256 | 22 | 296 | 19 | 337 | 23 |
| 26 | 50 | 67 | 48 | 257 | 31 | 297 | 19 | 338 | 16 |
| 27 | 67 | 68 | 70 | 258 | 30 | 298 | 27 | 339 | 16 |
| 28 | 54 | 69 | 54 | 259 | 27 | 299 | 28 | 340 | 31 |
| 29 | 33 | 70 | 155 | 260 | 35 | 300 | 29 | 341 | 27 |
| 30 | 65 | 71 | 314 | 261 | 36 | 301 | 28 | 342 | 27 |
| 31 | 44 | 72 | 53 | 262 | 33 | 302 | 22 | 343 | 23 |
| 32 | 67 | 73 | 21 | 263 | 26 | 303 | 21 | 344 | 21 |
| 33 | 45 | 74 | 52 | 264 | 27 | 304 | 26 | 345 | 31 |
| 34 | 44 | 75 | 44 | 265 | 24 | 305 | 18 | 346 | 26 |
| 35 | 52 | 76 | 62 | 266 | 40 | 306 | 26 | 347 | 23 |
| 36 | 85 | 77 | 212 | 267 | 31 | 307 | 26 | 348 | 20 |
| 37 | 57 | 78 | 539 | 268 | 24 | 308 | 22 | 349 | 27 |
| 38 | 85 | 79 | 48 | 269 | 39 | 309 | 12 | 350 | 25 |
| 39 | 37 | 80 | 20 | 270 | 26 | 310 | 22 | | |
| 40 | 50 | 81 | 43 | 271 | 35 | 311 | 17 | | |
| 41 | 65 | 82 | 53 | | | 312 | 28 | | |

As shown in Tables 2 and 3, lower than normal levels of G3P and GPX+G3P were found in each of the patients with breast carcinoma. The concentration of G3P in patients with breast carcinoma ranged from 2.8 to 16.2 µM. The concentration of G3P in normal patients ranged from 3.2 to 89.9 µM. The concentration of GPX+G3P in patients with breast carcinoma ranged from 12 to 40 µM. The concentration of GPX+G3P in normal patients ranged from 18 to 539 µM. Moreover, the average concentration of G3P or GPX+G3P in the serum of patients diagnosed as having breast carcinoma was significantly lower than the average concentration of G3P in the serum of healthy patients. These results establish that the present method is highly sensitive and therefore useful for identifying those patients with the carcinoma of breast carcinoma.

Various publications are cited herein which are hereby incorporated by reference in their entirety.

As will be apparent to those skilled in the art in which the invention is addressed, the present invention may be embodied in forms other than those specifically disclosed above without departing from the spirit or potential characteristics of the invention. Particular embodiments of the present invention described above are therefore to be considered in all respects as illustrative and not restrictive. The scope of the present invention is as set forth in the appended claims and equivalents thereof rather than being limited to the examples contained in the foregoing description.

We claim:

1. A method for diagnosing an ovarian carcinoma in a patient, comprising:
    i) collecting a specimen selected from the group consisting of a serum, plasma, and urine specimen;
    ii) measuring a concentration of endogenous glycerol-3-phosphate in the specimen;
    iii) correlating the concentration of endogenous glycerol-3-phosphate in the specimen with a concentration for a normal state or for an active ovarian carcinoma.

2. The method of claim 1, wherein the step of measuring the concentration of endogenous glycerol-3-phosphate comprises at least one enzymatic reaction.

3. The method of claim 2, wherein the measuring step utilizes glycerol-3-phosphate dehydrogenase.

4. The method of claim 2, wherein the measuring step utilizes glycerol-3-phosphate oxidase.

5. The method of claim 1, wherein the measuring step comprises an enzymatic cycling reaction utilizing glycerol-3-phosphate dehydrogenase and glycerol-3-phosphate oxidase.

* * * * *